(12) United States Patent
Talingting-Pabalan et al.

(10) Patent No.: US 7,494,944 B2
(45) Date of Patent: Feb. 24, 2009

(54) METHOD FOR DURABLE HYDROPHILIZATION OF A HYDROPHOBIC SURFACE

(75) Inventors: Ruela Talingting-Pabalan, Burlington, NJ (US); Mikel Morvan, Princeton, NJ (US); Gilda Lizarraga, Cranbury, NJ (US); Olivier Theodoly, Princeton, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/298,003

(22) Filed: Dec. 9, 2005

(65) Prior Publication Data

US 2006/0154544 A1 Jul. 13, 2006

(51) Int. Cl.
*B32B 3/12* (2006.01)
*B32B 27/00* (2006.01)
*A61F 13/15* (2006.01)

(52) U.S. Cl. .................. 442/118; 604/358; 442/394

(58) Field of Classification Search ............... 442/118, 442/394
See application file for complete search history.

(56) References Cited

U.S. PATENT DOCUMENTS

| | | | | |
|---|---|---|---|---|
| 4,535,098 A | * | 8/1985 | Evani et al. ............... | 521/149 |
| 5,137,633 A | * | 8/1992 | Wang ....................... | 210/490 |
| 5,591,149 A | * | 1/1997 | Cree et al. ................. | 604/378 |
| 5,945,175 A | * | 8/1999 | Yahiaoui et al. ............ | 427/534 |
| 6,437,040 B2 | | 8/2002 | Anthony et al. | |
| 6,974,660 B2 | | 12/2005 | Manias et al. | |
| 7,011,930 B2 | | 3/2006 | Manias et al. | |

FOREIGN PATENT DOCUMENTS

| WO | WO 01/78907 A1 | 10/2001 |
|---|---|---|
| WO | WO 03/064754 A1 | 8/2003 |

OTHER PUBLICATIONS

Schauer, T., "Organic polymer treatment—the way to modern pigments," International Union of Pure and Applied Chemistry, pp. 1-9 (1999).

* cited by examiner

*Primary Examiner*—Lynda Salvatore

(57) ABSTRACT

A method for hydrophilizing a hydrophobic surface of a substrate includes the steps of (a) defining a temperature range of: (i) greater than or equal to an anticipated lower use temperature (LUT), or (ii) less than or equal to an anticipated upper use temperature (UUT), or (iii) from a LUT to an UUT, wherein LUT≦UUT, within which the substrate is intended to be used in the presence of water, and (b) depositing at least one polymer on at least a portion of the surface, said polymer being soluble in water to the extent that an aqueous solution of such polymer exhibits: (i) a lower critical solution temperature (LCST), wherein LCST<LUT, or (ii) an upper critical solution temperature (UCST), wherein UUT<UCST, or (iii) a LCST and a UCST, wherein UCST<LCST and: (1) LCST<LUT, or (2) UUT<UCST.

28 Claims, No Drawings

METHOD FOR DURABLE HYDROPHILIZATION OF A HYDROPHOBIC SURFACE

FIELD OF THE INVENTION

This invention relates to methods for hydrophilizing hydrophobic substrates, more particularly to a method for durable hydrophilization of a hydrophobic surface.

BACKGROUND OF THE INVENTION

Materials that have a low surface energy, such as, for example, polyolefin polymers, have hydrophobic surfaces. The hydrophobic properties of such materials are not desirable in some applications and methods for hydrophilizing low surface energy substrates, including treatment with surfactants and/or high energy treatment, are known. Each of these methods has significant limitations. Surfactant treatments tend to wash off when a treated substrate is exposed to water and the charges imparted to the surface of a treated substrate by high energy treatment tend, particularly in the case of a thermoplastic polymer substrate, to dissipate. The hydrophilic properties of such surfactant treated substrates and high energy treated substrates thus tend to exhibit limited durability. Furthermore, the surfactants that are rinsed off of a treated substrate by exposure to water alter the properties of the water, such as lowering the surface tension, which may also be undesirable.

Hydrophilized polyolefin fabrics are used in some products, including disposable absorbent articles, such as diapers, adult incontinence products, wipes, and feminine hygiene products, wherein a hydrophilic surface is desirable, but the durability of the hydrophilic properties of such properties is limited, due to the limitations of available hydrophilization techniques.

Accordingly, there is a need for more durably hydrophilizing low surface energy substrates.

SUMMARY OF THE INVENTION

In a first aspect, the present invention is directed to a method for hydrophilizing a hydrophobic surface of a substrate, comprising:
(a) defining a temperature range of:
  (i) greater than or equal to an anticipated lower use temperature (LUT), or
  (ii) less than or equal to an anticipated upper use temperature (UUT), or
  (iii) from a LUT to an UUT, wherein LUT≦UUT,
  within which the substrate is intended to be used in the presence of water, and
(b) depositing at least one polymer on at least a portion of the surface, said polymer being soluble in water to the extent that an aqueous solution of such polymer exhibits:
  (i) a lower critical solution temperature (LCST), wherein LCST<LUT, or
  (ii) an upper critical solution temperature (UCST), wherein UUT<UCST, or
  (iii) a LCST and a UCST, and:
    (1) LCST<LUT, or
    (2) UUT<UCST.

In a second aspect, the present invention is directed to a hydrophilized fabric intended for use in the presence of water within a temperature range of greater than or equal to an anticipated lower use temperature (LUT), or less than or equal to an anticipated upper use temperature (UUT), or from a LUT to an UUT, wherein LUT≦UUT, comprising:
(a) a fabric substrate comprising fibers having hydrophobic surfaces, and
(b) at least one polymer deposited on at least a portion of the fiber surfaces, said polymer being soluble in water to the extent that an aqueous solution of such polymer exhibits:
  (i) a lower critical solution temperature (LCST) of less than the LUT,
  (ii) an upper critical solution temperature (UCST) of greater than the UUT, or
  (iii) a LCST of less than the LUT and a UCST of greater than the UUT.

In a third aspect, the present invention is directed to a disposable absorbent article intended for use in the presence of water within a temperature range of greater than or equal to an anticipated lower use temperature (LUT), or less than or equal to an anticipated upper use temperature (UUT), or from a LUT to an UUT, wherein LUT≦UUT, comprising a hydrophilized fabric, said fabric comprising:
(a) a fabric substrate comprising fibers having hydrophobic surfaces, and
(b) at least one polymer deposited on at least a portion of the fiber surfaces, said polymer being soluble in water to the extent that an aqueous solution of such polymer exhibits:
  (i) a lower critical solution temperature (LCST) of less than the LUT,
  (ii) an upper critical solution temperature (UCST) of greater than the UUT, or
  (iii) a LCST of less than the LUT and a UCST of greater than the UUT.

In a fourth aspect, the present invention is directed to a disposable absorbent article selected from diapers, adult incontinence products, wipes, and feminine hygiene products, comprising at least one fabric substrate, said fabric substrate comprising fibers having hydrophobic surfaces and at least one polymer deposited on at least a portion of the fiber surfaces, said polymer being soluble in water to the extent that an aqueous solution of such polymer exhibits a lower critical solution temperature of less than 20° C.

DETAILED DESCRIPTION OF INVENTION

As used herein, "hydrophobic surface" means a surface that is not wettable by water, as evidenced by a contact angle with water of greater than or equal to 70°, more typically greater than or equal to 90°, "hydrophilic surface" means a surface that is wettable by water, as evidenced by a contact angle with water of less than 70°, more typically less than 60° C., and "hydrophilizing" a hydrophobic surface means rendering the surface less hydrophobic, as indicated by a decreased contact angle with water, wherein in each case, the contact angle with water is measured by a conventional image analysis method, that is, by disposing a droplet of water on the substrate at 25° C., photographing the droplet, and measuring the contact angle shown in the photographic image.

As used herein, "lower use temperature" means the lowest temperature at which it is anticipated that a substrate will be used in contact with water, and "upper use temperature" means the highest temperature at which it is anticipated that a substrate will be used in contact with water.

As used herein, "cloud point" means the temperature at which a water solution of a thermally responsive polymer exhibits phase separation. In some cases (wherein the cloud point is termed an "upper critical solution temperature" or "UCST"), the polymer is soluble and forms a clear, single phase solution at temperatures greater than the UCST and the polymer becomes at least partially insoluble and the solution separates into two phases and becomes turbid at temperatures at or below the UCST. In other cases (wherein the cloud point is termed a "lower critical solution temperature" or "LCST"), the polymer is soluble and forms a clear, single phase solution at temperatures less than the LCST and the polymer becomes insoluble and the solution separates into two phases and becomes turbid at temperatures at temperatures at or above the LCST. The cloud point, LCST, and UCST are measured by visual detection of turbidity as a 1 percent by weight ("wt %") aqueous polymer solution is heated or cooled at a controlled rate, typically, a rate of about 1° C./5 minutes, as compared to a sample of water. The technique can be refined by heating or cooling the solution to detect an apparent cloud point and then alternately heating and cooling the sample within a temperature range that includes the apparent cloud point to detect both the appearance and the disappearance of turbidity.

Suitable substrates are those that exhibit at least one hydrophobic surface and include, for example, poly(methyl methacrylate), polystyrene poly(olefin) materials, such as poly (ethylene) and poly(propylene), and polyamide materials, polyacrylonitrile, and polyethyleneterephthalate.

The substrate may be in any physical shape or configuration, such as for example, particles, sheets, films, fibers, extruded profiles, woven fabrics, and non-woven fabrics.

In one embodiment, the substrate comprises fibers having hydrophobic surface, and more typically, the substrate is a woven or non-woven fabric comprising such fibers.

In one embodiment, the substrate comprises a nonwoven material in a web format made from fibers having hydrophobic surfaces. Nonwoven materials are well know, see, for example, Butler I., et. al., *Nonwovens Fabric Handbook*, Assoc. of the Nonwoven Fabrics Industry (1999).

Nonwoven webs are typically formed by direct extrusion processes, such as spunbonding, meltblowing, solvent spinning, or electrospinning, in which the fibers and web are formed simultaneously, or by preformed fiber processes, such as dry laying or wet laying, in which fibers are laid into webs at a time subsequent to fiber formation, or by combinations of such processes, such as by spunbond-meltblown-spunbond, spunbond-airlaid, and meltblown-airlaid processes.

At least a portion of the fibers of a nonwoven web are typically oriented with some non-zero angle relative to other fibers of the web. Places were two or more fibers touch, in either an adjacent or overlapping manner, are called junctions. The fibers of a nonwoven web are typically joined to one or more of the other fibers of the web, by, for example, thermal bonding, pressure bonding, ultrasonic bonding, or solvent bonding, at at least some of the junctions.

Nonwoven webs may be joined with other materials, to form composite materials. In one embodiment, nonwoven webs are stacked to form a nonwoven laminate material. In another embodiment, one or more nonwoven webs are stacked with one or more other materials, such as porous films or non porous films, to form composite laminate substrates.

The polymer used in the present method may be a homopolymer or a copolymer. Suitable polymers include linear polymers, branched polymers, star polymers, and comb polymers. Suitable copolymers include random copolymers, alternating copolymers, block copolymers, and graft copolymers.

As used herein, each of the terms "monomer", "polymer", "homopolymer", "copolymer", "linear polymer", "branched polymer", "star polymer", "comb polymer", "random copolymer", alternating copolymer", "block copolymer", "graft copolymer", has the meaning ascribed to it in *Glossary of basic terms in polymer science* (IUPAC Recommendations 1996), *Pure Appl. Chem.*, Vol. 68, No.12, pp. 2287-2311, 1996.

In one embodiment, the polymer is a homopolymer. Suitable homopolymers are known and include, for example, poly(N-ethyl acrylamide), reportedly having an LCST of about 72° C., poly(N-cyclobutane acrylamide), reportedly having an LCST of about 56° C., poly(N-ethyl methacrylamide), reportedly having an LCST of about 50° C., poly(N-isopropyl methacrylamide), reportedly having an LCST of about 45° C., poly(vinyl methyl ether), reportedly having an LCST of about 38° C., poly(N,N'-diethyl acrylamide), reportedly having an LCST of about 32° C., poly(N-isopropyl acrylamide), reportedly having an LCST of about 31° C., poly(N-n-propyl methacrylamide), reportedly having an LCST of about 28° C., poly(N-n-propyl acrylamide), reportedly having an LCST of about 21.5° C., and poly(N-N-cyclopentane acrylamide), reportedly having an LCST of about 5.5° C., and poly(propylene glycol) reportedly having an LCST of from about 15° C. to about 42° C., depending on molecular weight.

In another embodiment, the polymer is a copolymer. Suitable copolymers are known and include, for example, a random poly(isopropylacrylamide ("niPAM") co-N-butylacrylamide ("nBAM")) copolymer comprising 60% niPAM, which reportedly has an LCST of about 8.5° C., a random poly(niPAM-co-nBAM) copolymer comprising 80% niPAM, which reportedly has an LCST of about 18.5° C., and a random poly(niPAM-co-vinyl saccharide) comprising 13.7% vinyl saccharide, which reportedly has an LCST of about 42° C.

In general, polymers that exhibit a cloud point are believed to form hydrogen bonds with water. Suitable polymers typically comprise one or more hydrophilic moieties and one or more hydrophobic moieties per molecule of the polymer, more typically a plurality of hydrophilic moieties and a plurality of hydrophobic moieties per molecule of the polymer.

As used herein, "hydrophilic moiety" means a moiety, such as a hydroxyl group, a $(C_2-C_3)$alkyleneoxide group, an ester moiety, or an amide moiety, that has a tendency to bind or absorb water and "hydrophobic moiety" means a moiety, such as an alkyl group, an aromatic moiety, a fluoroalkyl group, or a dimethylsiloxyl group, that does not tend to bind or absorb water.

The cloud point of an aqueous solution of such a polymer is influenced by the relative amounts of hydrophilic moieties and hydrophobic moieties of the polymer. The balance of hydrophilic and hydrophobic moieties effective to provide a desired cloud point is typically empirically determined, that is, by studying the solubility of candidate polymers in water over a range of temperatures.

Suitable polymers, including polymers that provide a desired cloud point, may be developed by empirical methods. For example, a polymer, or, more typically a series of analogous polymers wherein the relative amounts of hydrophilic moieties and hydrophobic moieties are systematically varied, may be synthesized and subjected to cloud point measurement.

As a guideline for designing such polymers, the monomeric units of such polymers can be roughly characterized, based on the solubility in water at 25° C. at a concentration of 1 wt %, of a homopolymer of such units, as having a primarily hydrophilic character or a primarily hydrophobic character. Such characterization is an oversimplification, since it does not take the effect of changing temperature on the solubility of such homopolymers and does not distinguish those monomeric units that form homopolymers having a cloud point, that is, a homopolymer that is soluble at 25° C. may simply be below its LCST or above its UCST.

As used herein, the term "hydrophilic monomeric units" are those wherein homopolymers of such monomeric units are soluble in water at 25° C. at a concentration of 1 wt % homopolymer, and include, for example, monomeric units derived from, for example, hydroxy($C_1$-$C_4$)alkyl (meth)acrylates, (meth)acrylamide, ($C_1$-$C_4$)alkyl (meth)acrylamides, N,N-dialkyl-acrylamides, alkoxylated (meth)acrylates, poly (ethylene glycol)-mono methacrylates and poly(ethyleneglycol)-monomethylether methacrylates, hydroxy($C_1$-$C_4$)acrylamides and methacrylamides, hydroxyl($C_1$-$C_4$)alkyl vinyl ethers, N-vinylpyrrole, N-vinyl-2-pyrrolidone, 2- and 4-vinylpyridine, ethylenically unsaturated carboxylic acids having a total of 3 to 5 carbon atoms, amino($C_1$-$C_4$)alkyl, mono ($C_1$-$C_4$)alkylamino($C_1$-$C_4$)alkyl, and di($C_1$-$C_4$)alkylamino ($C_1$-$C_4$)alkyl (meth)acrylates, allyl alcohol, dimethylaminoethyl methacrylate, dimethylaminoethylmethacrylamide.

As used herein, the term "(meth)acrylate" means acrylate, methacrylate, or acrylate and methacrylate and the term (meth)acrylamide" means acrylamide, methacrylamide or acrylamide and methacrylamide. As used herein, the notation "($C_n$-$C_m$)" in reference to an organic group or compound, wherein n and m are integers, means that the group or compound contains from n to m carbon atoms per such group or compound.

As used herein, the term "hydrophobic monomeric units" are those wherein homopolymers of such monomeric units are insoluble in water at 25° C. at a concentration of 1 wt % homopolymer, and include, for example, monomeric units derived from ($C_1$-$C_{18}$)alkyl and ($C_5$-$C_{18}$)cycloalkyl(meth) acrylates, ($C_5$-$C_{18}$)alkyl(meth)acrylamides, (meth)acrylonitrile, vinyl ($C_1$-$C_{18}$)alkanoates, ($C_2$-$C_{18}$)alkenes, ($C_2$-$C_{18}$)haloalkenes, styrene, ($C^1$-$C_6$)alkylstyrenes, ($C_4$-$C_{12}$)alkyl vinyl ethers, fluorinated ($C_2$-$C_{10}$)alkyl(meth)acrylates, ($C_3$-$C_{12}$) perfluoroalkylethylthiocarbonylaminoethyl (meth)acrylates, (meth)acryloxyalkylsiloxanes, N-vinylcarbazole, ($C_1$-$C_{12}$) alkyl maleic, fumaric, itaconic, and mesaconic acid esters, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate, and 3-methacryloxypropylpentamethyldisiloxane.

In one embodiment, the polymer is a homopolymer, wherein each monomeric unit of the homopolymer comprises a hydrophilic moiety and a hydrophobic moiety.

In one embodiment, the polymer is a copolymer, derived from two or more copolymerizable monomers. In one embodiment, at least one of such copolymerizable monomers is a monomer that forms a homopolymer having a cloud point. In another embodiment, at least one of the copolymerizable monomers is selected from hydrophilic monomer and at least one of the copolymerizable monomers is selected from hydrophobic monomers.

The cloud point of such copolymers can be varied by controlling the relative amounts of the monomeric units of the copolymer. For example, given a copolymer having an LCST, the LCST of an analogous copolymer can typically be increased by increasing the relative amount of hydrophilic monomeric units in the analogous copolymer or decreased by increasing the relative amount of hydrophobic monomeric units in the analogous copolymer. This approach is illustrated in, for example Rackaitis, M., Strawhecker, K. and Manias, E., "Water Soluble Polymers with Tunable Temperature Sensitivity: Solution Behavior", J. Polym. Sci. Part B: Polm. Phys., 2339 Vol. 40 (2002).

In one embodiment, the polymer comprises one or more monomeric units derived from at least one monomer according to formula (I):

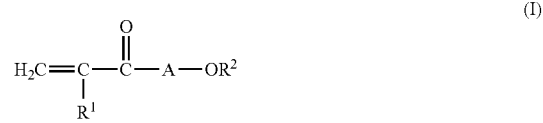

wherein:
$R^1$ is H or methyl,
A is oxyalkylene or poly(oxyalkylene), and
$R^2$ is alkyl more typically ($C_1$-$C_6$)alkyl.

As used herein, "oxyalkylene" means a divalent radical according to formula (II):

wherein $R^3$ is a straight or branched alkylene group, typically a ($C_1$-$C_3$)alkylene group, such as for example, oxethylene, or oxypropylene, and "poly(oxyalkylene)" means a chain of oxyalkylene units according to formula (III):

wherein each $R^4$ is independently $R^3$ and $1 \leq n' \leq 50$, more typically, $2 \leq n \leq 25$.

In one embodiment, n is greater than or equal to 9 and $R^2$ is $(CH_2)_{m'}CH_3$, wherein m' is from 1 to 5.

Monomers according to formula (I) include, for example: diethyleneglycolethyletheracrylate ("DEGA"), diethyleneglycolethylethermethacrylate ("DEGMA"), nonethyleneglycolmethyletheracrylate ("nEGA"), nonethyleneglycolmethylethermethacrylate ("nEGMA").

In one embodiment, the polymer comprises one or more monomeric units derived from at least one monomer according to formula (IV):

wherein:
$R^5$ is H or methyl,
each $R^6$ is independently H or alkyl, more typically H or ($C_1$-$C_6$)alkyl.

Monomers according to formula (V) include, for example: isopropylacrylamide (niPAM), N-butylacrylamide (nBAM).

In one embodiment, the polymer is a homopolymer derived from a monomer according to formula (I) or (IV), such as poly(DEGA), poly(DEGMA), poly(nEGA), poly(NEGMA), and poly(niPAM).

In one embodiment, the polymer is a copolymer comprising monomeric units derived from a monomer according to formula (I) or (IV), more typically wherein greater than or equal to about 50 percent by weight ("wt %") of the monomeric units of the polymer are derived from a monomer according to formula (I) or (IV).

In one embodiment, the molecular weight of the polymer, is from about 1,000 to about 1,000,000 Daltons, more typically, from about 1,000 to about 200,000 Daltons, and even more typically, from about 1,000 to about 50,000 Daltons. As used herein, "molecular weight" in reference to a polymer or any portion thereof, means to the weight-average molecular weight ("$M_w$") of said polymer or portion, wherein $M_w$ of a polymer is a value measured by gel permeation chromatography and $M_w$ of a portion of a polymer is a value calculated according to known techniques from the amounts of monomers, polymers, initiators and/or transfer agents used to make the said portion.

Methods for making suitable polymers are known in the art.

In one embodiment, the polymer is made by known free radical polymerization processes using ethylenically unsaturated monomers.

In another embodiment, the polymer is made by known controlled free radical polymerization techniques, such as reversible addition fragmentation transfer (RAFT), macromolecular design via interchange of xanthates (MADIX), and atom transfer reversible polymerization (ATRP).

The polymer may be deposited on the hydrophobic surface of the substrate by, for example, spraying the polymer or a solution of the polymer onto the substrate, immersing the substrate in the polymer or in a solution of the polymer.

In one embodiment, the polymer is deposited on hydrophobic surface by applying, such as, for example, by spraying, an aqueous solution of the polymer to at least a portion of the surface and then evaporating the aqueous component of the solution.

In one embodiment, the polymer is deposited by contacting at least portion of the surface with an aqueous solution of the polymer at a first temperature ($T_1$), and changing the temperature of the solution to a second temperature ($T_2$) while the solution remains in contact with the substrate to precipitate at least a portion of the polymer onto the surface of the substrate, wherein:

(i) $T_1 < LCST < T_2 < LUT$, or
(ii) $UUT < T_2 < UCST < T_1$.

In one embodiment, the treated surface exhibits improved wettability with water, as indicated by decreased contact angle with water droplets. Typically the treated substrate exhibits a contact angle of less than 90°, more typically less than 70°.

The hydrophilic treatment of the present invention is highly durable within the defined temperature range within which the substrate is intended to be used in the presence of water. For applications wherein the substrate is exposed to water only at temperatures above the LCST of the polymer or only at temperatures below the UCST of the polymer, the hydrophilic treatment is highly resistant to being rinsed off in the water. Typically, the hydrophilic properties of the surface survive many water rinses.

In one embodiment, the substrate, hydrophilized fabric, or disposable absorbent article of the present invention is intended to be used in contact with water within a temperature range of greater than or equal to 20° C. and the polymer exhibits a LCST of less than 20° C., more typically less than or equal to 15° C.

In one embodiment, the substrate, hydrophilized fabric, or disposable absorbent article of the present invention is intended to be used in contact with water within a temperature range of greater than or equal to 25° C. and the polymer exhibits a LCST of less than 25° C., more typically less than or equal to 20° C.

In one embodiment, the substrate, hydrophilized fabric, or disposable absorbent article of the present invention is intended to be used in contact with water within a temperature range of greater than or equal to 30° C. and the polymer exhibits a LCST of less than 30° C., more typically less than or equal to 25° C.

In one embodiment, the substrate, hydrophilized fabric, or disposable absorbent article of the present invention is intended to be used in contact with water within a temperature range of less than or equal to 40° C. and the polymer exhibits a UCST of greater than 40° C., more typically greater than or equal to 45° C.

In one embodiment, the substrate is a woven or nonwoven fabric comprising fibers having hydrophobic surfaces, such as for example, poly(olefin) fibers, the hydrophobic surfaces of which are rendered hydrophilic to allow the fabric to absorb water.

In one embodiment, the fabric substrate of the hydrophilized fabric of the present invention is a porous nonwoven fabric substrate, more typically a nonwoven poly(olefin) fabric substrate, even more typically nonwoven poly(propylene) fabric substrate.

In one embodiment, hydrophilized fabric of the present invention comprises a nonwoven laminate material that comprises the porous nonwoven fabric substrate.

In one embodiment, the hydrophilized fabric is a component of a disposable absorbent article.

In one embodiment, the hydrophilized fabric of the present invention is intended to be used in contact with water temperatures greater than or equal to about 20° C., more typically from about 25° C. to about 40° C., even more typically from about 30° C. to about 40° C.

In one embodiment, the fabric substrate of the disposable absorbent article of the present invention is a porous nonwoven fabric substrate, more typically a nonwoven polyolefin fabric substrate, even more typically nonwoven poly(propylene) fabric substrate.

In one embodiment, the disposable absorbent article comprises a nonwoven laminate material that comprises the porous nonwoven fabric substrate.

In one embodiment, the disposable absorbent article comprises a composite laminate material, comprising one or more layers of the porous nonwoven fabric substrate and one or more polymer films.

In one embodiment, the disposable absorbent article comprises a composite laminate material, comprises one or more layers of the porous nonwoven fabric substrate, a nonporous polymer film, and an adsorbent material, such as, for example, a polyacrylate adsorbent material, disposed between the porous nonwoven fabric substrate and the nonporous film.

In one embodiment, the disposable absorbent article is intended to be used in contact with water temperatures greater than or equal to about 20° C., more typically from about 25° C. to about 40° C., even more typically from about 300C to about 40° C.

In one embodiment, the disposable absorbent article of the present invention is selected from diapers, adult incontinence products, wipes, and feminine hygiene products, and comprises at least one nonwoven fabric substrate, wherein the nonwoven fabric substrate comprises fibers having hydrophobic surfaces and at least one polymer that comprises monomeric units derived from diethyleneglycolethyletheracrylate and exhibits a lower critical solution temperature of less than 20° C. deposited on at least a portion of the hydrophobic surfaces. In one embodiment, the polymer is a poly (diethyleneglycolethyletheracrylate) homopolymer. The polymer deposited on the hydrophilic surface hydrophilizes the surface.

In one embodiment, the disposable absorbent article of the present invention has a composite laminate structure and comprises one or more layers of a hydrophilized porous nonwoven fabric according to the present invention and one or more layers of a nonporous polymer film, such as a nonporous poly(olefin) film.

In one embodiment, the disposable absorbent article according to the present invention is an article, such as a diaper, an adult incontinence product, or a feminine hygiene product, for absorbing aqueous physiological fluids, such as urine. In one embodiment, such disposable absorbent article has a composite laminate structure and comprises at least one layer of a porous hydrophilized fabric, typically a porous hydrophilized nonwoven fabric, at least one layer of a nonporous water impermeable film, such as a nonporous poly(olefin) film, and at least one layer of an adsorbent material, typically a superabsorbent material, disposed between the layer of porous hydrophilized fabric and the layer of nonporous water impermeable film.

As used herein, the term "super-absorbent material" refers to a water-swellable, water-insoluble organic or inorganic material capable, under favorable conditions, of absorbing at least several times, preferably at least 10 times and most preferably at least 30 times, its weight in an aqueous solution containing about 0.9 weight percent of sodium chloride. Suitable superabsorbent materials are generally known. Organic materials suitable for use as a super-absorbent material of the present invention can include natural materials such as agar, pectin, guar gum, and modified natural materials such as the sodium salt of carboxymethylcellulose, as well as synthetic materials such as synthetic hydrogel polymers. Such hydrogel polymers include, for example, alkali metal salts of polyacrylic acids, partially-neutralized polyacrylamides, ethylene maleic anhydride copolymers, and polymers and copolymers of vinyl sulfonic acid, polyacrylates, polyacrylamides, and polyvinyl pyridines. Other suitable polymers include hydrolyzed acrylonitrile grafted starch, acrylic acid grafted starch, and isobutylene maleic anhydride copolymers and mixtures thereof. Examples of polymer materials suitable for use include those comprising monomeric units derived from polymerizable, unsaturated, acid-containing monomers, such as ethylenically unsaturated carboxylic acids, such as acrylic acid or methacrylic acid, acid anhydrides, such as maleic anhydride, ethylenically unsaturated sulfonic acids, and mixtures thereof and optionally further comprising monomeric units derived from non-acid-containing monomers, such as ethylenically unsaturated carboxylic acid ester monomers or ethylenically unsaturated sulfonic acid ester monomers. Other polymer materials for use in the present invention possess a carboxyl group. These polymers include hydrolyzed starch-acrylonitrile graft copolymer, partially neutralized starch-acrylonitrile graft copolymer, starch-acrylic acid graft copolymer, partially neutralized starch-acrylic acid graft copolymer, saponified vinyl acetate-acrylic ester copolymers, hydrolyzed acrylonitrile or acrylamide copolymers, lightly crosslinked products of any of the foregoing copolymers, partially neutralized polyacrylic acid, and slightly network crosslinked products of partially neutralized polyacrylic acid. These polymers may be used either independently or in the form of mixtures with other polymers.

The superabsorbent material is typically present in the form of composite material comprising a granular superabsorbent particulate, typically sized between 100 microns and 1000 microns dispersed in a permeable meshwork that spaces the super-absorbent particles from each other, provides cushioning, provides open voids to permeate and transfer liquid through the composite material, and provides strength to the composite material as a whole. The permeable meshwork may comprise a natural material or a synthetic polymer and typically comprises cellulose fluff. Cellulose fluff is made of cellulose fibers obtained from wood-pulping processes and is commonly used in absorption applications where strands of the fibers are loosely intertwined to provide a meshwork having a greater volumetric percentage of open void than of intertwined strands.

In use, the layer of hydrophilized fabric of the disposable absorbent article is oriented toward the user, typically the wearer, of the disposable absorbent article. Aqueous physiological fluid that may be produced by the user flow tends to flow through the porous hydrophilized fabric layer into the absorbent layer. The nonporous water impermeable film provides a barrier against leakage from the absorbent layer.

In one embodiment, the disposable absorbent article is a wipe that comprises one or more layers, each independently comprising a hydrophilized woven fabric or a hydrophilized nonwoven fabric.

EXAMPLE 1

The polymer of Example 1 was made as follows. Ethanol (32.00 grams ("g")), di ethylene glycol ethyl ether acrylate (Aldrich CAS 7328-17-8, 50.00 g), xanthate A (1.041 g), and AIBN (0.280 g) are charged into a 250-ml polymerization bottle with a mechanic stirrer. After sealing the cap with the rubber septum, the contents are bubbled through dry nitrogen for 60 minutes, then heated to 70° C. and held at this temperature for 8 hours. Small amount of sample is withdrawn to check the conversion by gas chromatography head-space. At the end, the solid content is 20 wt %.

The polymer of Example 1 had a lower critical solution temperature of about 9° C., as determined by visual detection of the turbidity of a 1 wt % aqueous solution of the polymer while cooling the solution from 25° C. to 5° C. at a rate of 1° C. per 5 minutes.

EXAMPLE 2

The treated substrate of Example 2 was made as follows.

A 30 cm×20 cm piece of nonwoven poly(propylene) fabric (having a weigh about 17 grams per square meter of fabric and an average thickness of about 0.12 millimeters ("mm")) was cut, marked to distinguish upper side to be treated, weighed, and placed against an aluminum foil. Gloves were worn during all handling of the fabric 30 mL of 0.1 wt % solution of the polymer of Example 1 in water was prepared and cooled to about 10° C. in a refrigerator. The cool solution was removed from refrigerator and a tube equipped with nozzle sprayer tool was introduced into the solution. The solution was then sprayed onto the nonwoven fabric until the fabric was slightly damp. The dampened fabric was then dried with warm air using an airgun, cooled to room temperature, and weighed.

The treated substrate of Example 2 was evaluated by rinsing in water and measuring the surface tension of rinse water according to ASTM 1331 (except as specifically noted below). A 20×18 cm sample (360 cm² total area) was cut from the treated fabric. The fabric sample was placed onto 40 milliliters ("mL") of a 0.909 wt % NaCl aqueous solution and the fabric was stirred in the solution for 10 seconds, was then allowed to sit without any agitation for 5 minutes, was then stirred for 10 seconds, and was then removed from the solution. The solution was allowed to rest for 10 minutes and then the surface tension of the solution was determined to be 61 milliNewtons per meter ("mN/m") using a Wilhemy plate (Kruss Instruments). The surface tension of 0.909 wt % aqueous NaCl is about 71 mN/m and the surface tension of a 0.1 wt % aqueous solution of poly(DEGA) was found to be about 40 mN/m. The result indicated that very little poly(DEGA) was present in the aqueous solution.

The treated substrate of Example 2 was evaluated by a "strikethrough" test according to EDANA test 150.3-96 (except as specifically noted below). A 12×12 cm sample of treated fabric was placed on top of a filter paper and 10 lab paper towels, with the treated side fabric facing up, and placed under a 50 mL separatory funnel. A burette was filled with 0.909 wt % NaCl up to 50 mL. Making sure that the funnel stopcock was closed, a 5 mL aliquot of the saline solution was delivered from the burette to the funnel. The funnel stopcock was opened and the time from the moment the liquid touched the fabric until all liquid disappears onto the paper (the "strikethrough time") was measured. The strikethrough time for the first aliquot was about 3 seconds. After 60 seconds, a second 5 mL aliquot of the saline solution was introduced to the fabric sample. The procedure was repeated three more times. The strikethrough time for each of the aliquots was about 3 seconds. The strikethrough time with just filter paper alone, without the fabric, was also measure and found to be about 3 seconds.

EXAMPLE 3

A 1 inch×1 inch piece of polypropylene plastic plaque (of about 2 mm thick) was cut, washed 60° C. with acetone/methanol mixture for one hour, and dried with pure nitrogen. The clean plaque was placed between two glass slides (cleaned with the same hot acetone/methanol mixture for an hour). A weight (about 500 g) was placed on top of the slides and the set-up is placed inside an oven and heated to 165° C. for about 3 hours to flatten and smooth the surface of the plaque. The assembly was then allowed to cool down slowly and the plaque was removed from between the glass slides and rinsed again with hot acetone/methanol for an hour. The plaque was then placed on a Petri dish ready for further treatment. Gloves were worn during all handling of the plaque.

30 mL of 1 wt % solution of the polymer of Example 1 in water was prepared and cooled to about 10° C. in a refrigerator. The solution was then poured onto the polypropylene plaque (placed on a Petri dish) until it covered the entire surface of the plaque. The dish was then placed inside an oven at 60° C. for 30 minutes. The dish was then removed from the oven, the polymer solution was drained out of the dish, and the plastic was rinsed with deionized water. The treated plaque was then allowed to air-dry as it cooled to room temperature.

The treated plaque was evaluated by measuring contact angle of water using a conventional sessile drop method by image analysis of a water droplet on the surface. The contact angle for the non-treated plaque was 108°. The contact angle for the treated plaque was 50°.

The invention claimed is:
1. A hydrophilized fabric intended for use in the presence of water within a temperature range of greater than or equal to an anticipated lower use temperature (LUT), or less than or equal to an anticipated upper use temperature (UUT), or from a LUT to an UUT, wherein LUT≦UUT, comprising:
   (a) a fabric substrate comprising fibers having hydrophobic surfaces, and
   (b) at least one polymer deposited on at least a portion of the hydrophobic surfaces of the fibers, wherein the at least one polymer comprises monomeric units derived from at least one monomer according to formula (I) or (IV):

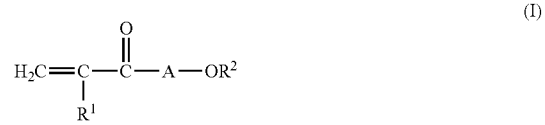

wherein:
   $R^1$ is H or methyl,
   A is oxyalkylene or poly(oxyalkylene), and
   $R^2$ is alkyl

wherein:
   $R^5$ is H or methyl,
   each $R^6$ is independently H or alkyl,
   and is soluble in water to the extent that an aqueous solution of such polymer exhibits:
   (i) a lower critical solution temperature (LCST) of less than the LUT,
   (ii) an upper critical solution temperature (UCST) of greater than the UUT, or
   (iii) a LCST of less than the LUT and a UCST of greater than the UUT.

2. A disposable absorbent article intended for use in the presence of water within a temperature range of greater than or equal to an anticipated lower use temperature (LUT), or less than or equal to an anticipated upper use temperature (UUT), or from a LUT to an UUT, wherein LUT≦UUT, comprising a hydrophilized fabric, said fabric comprising:
   (a) a fabric substrate comprising fibers having hydrophobic surfaces, and
   (b) at least one polymer deposited on at least a portion of the hydrophobic surfaces of the fibers, wherein the at least one polymer comprises monomeric units derived from at least one monomer according to formula (I) or (IV):

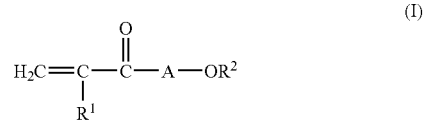

wherein:
   $R^1$ is H or methyl,
   A is oxyalkylene or poly(oxyalkylene), and
   $R^2$ is alkyl

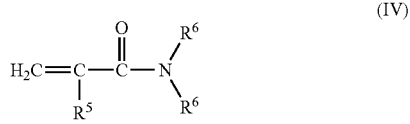

wherein:

R⁵ is H or methyl, each R⁶ is independently H or alkyl, and is soluble in water to the extent that an aqueous solution of such polymer exhibits:

(i) a lower critical solution temperature (LOST) of less than the LUT, (ii) an upper critical solution temperature (UCST) of greater than the UUT, or (iii) a LCST of less than the LUT and a UCST of greater than the UUT.

3. A disposable absorbent article selected from diapers, adult incontinence products, wipes, and feminine hygiene products, comprising at least one porous hydrophilized fabric substrate, said porous hydrophilized fabric substrate comprising fibers having hydrophobic surfaces and at least one polymer deposited on at least a portion of hydrophobic surfaces of the fibers, wherein the polymer comprises monomeric units derived from diethyleneglycolethyletheracrylate and is soluble in water to the extent that an aqueous solution of such polymer exhibits a lower critical solution temperature of less than 20° C.

4. The article of claim 3, wherein the polymer is a poly(diethyleneglycolethyletheracrylate) homopolymer.

5. The article of claim 3, wherein the article is a diaper, adult incontinence product or feminine hygiene product that comprises:
at least one layer of the porous hydrophilized fabric substrate,
at least one layer of a nonporous water impermeable film, and
at least one layer of an adsorbent material disposed between the layer of porous hydrophilized fabric and the layer of nonporous water impermeable film.

6. The article of claim 5, wherein fabric substrate is a nonwoven polyolefin fabric.

7. The article of claim 5, wherein the nonporous water impermeable film is a nonporous water impermeable poly(olefin) film.

8. The article of claim 5, wherein the absorbent material is a superabsorbent material that comprises a synthetic hydrogel polymer.

9. The article of claim 3 wherein the article is a wipe that comprises each of the one or more layers of porous hydrophilized fabric substrate independently comprises a porous hydrophilized woven fabric or a porous hydrophilized nonwoven fabric.

10. The fabric of claim 1, wherein the fibers comprise poly(olefin) fibers or polyamide fibers.

11. The fabric of claim 1, wherein the LUT is 20° C. and the at least one polymer exhibits a LCST of less than 20° C., or the UUT is 40° C. and the at least one polymer exhibits a UCST of greater than 40° C.

12. The fabric of claim 11, wherein the LUT is 20° C. and the at least one polymer exhibits a LCST of less than 20° C.

13. The fabric of claim 12, wherein the at least one polymer exhibits a LCST of less than 15° C.

14. The fabric of claim 1, wherein the at least one monomer is selected from the group consisting of diethyleneglycolethyletheracrylate, diethyleneglycolethylethermethacrylate, nonethyleneglycolmethyletheracrylate, and nonethyleneglycolmethylethermethacrylate.

15. The article of claim 2, wherein the fibers comprise poly(olefin) fibers or polyamide fibers.

16. The article of claim 2, wherein the LUT is 20° C. and the at least one polymer exhibits a LCST of less than 20° C. or the UUT is 40° C. and the at least one polymer exhibits a UCST of greater than 40° C.

17. The article of claim 16, wherein the LUT is 20° C. and the at least one polymer exhibits a LCST of less than 20° C.

18. The article of claim 17, wherein the at least one polymer exhibits a LCST of less than 15° C.

19. The article of claim 2, wherein the at least one monomer is selected from the group consisting of diethyleneglycolethyletheracrylate, diethyleneglycolethylethermethacrylate, nonethyleneglycolmethyletheracrylate, and nonethyleneglycolmethylethermethacrylate.

20. The article of claim 3, wherein the fibers comprise poly(olefin) fibers or polyamide fibers.

21. The hydrophilized fabric of claim 1, wherein the at least one monomer is according to formula (I), A is —(OR³)—, or —(OR⁴)n'—., R³ and R⁴ are each ($C_1$-$C_3$)alkylene, and n' is 2.

22. The hydrophilized fabric of claim 1, wherein the at least one monomer is selected from the group consisting of diethyleneglycolethyletheracrylate and diethyleneglycolethylethermethacrylate.

23. The hydrophilized fabric of claim 1, wherein the polymer is a homopolymer of diethyleneglycolethyletheracrylate, diethyleneglycolethylethermethacrylate, nonethyleneglycolmethyletheracrylate, or nonethyleneglycolmethylethermethacrylate.

24. The hydrophilized fabric of claim 1, wherein the polymer is a homopolymer of diethyleneglycolethyletheracrylate.

25. The disposable absorbent article of claim 2, wherein the at least one monomer is according to formula (I), A is —(OR³)—, or —(OR⁴)n'—., R³ and R⁴ are each ($C_1$-$C_3$)alkylene, and n' is 2.

26. The disposable absorbent article of claim 2, wherein the at least one monomer is selected from the group consisting of diethyleneglycolethyletheracrylate and diethyleneglycolethylethermethacrylate.

27. The disposable absorbent article of claim 2, wherein the polymer is a homopolymer of diethyleneglycolethyletheracrylate, diethyleneglycolethylethermethacrylate, nonethyleneglycolmethyletheracrylate, or nonethyleneglycolmethylethermethacrylate.

28. The hydrophilized fabric of claim 1, wherein the polymer is a homopolymer of diethyleneglycolethyletheracrylate.

* * * * *